US012313559B2

(12) United States Patent
Wolf et al.

(10) Patent No.: US 12,313,559 B2
(45) Date of Patent: May 27, 2025

(54) SYSTEM AND METHOD FOR DETECTING THE PRESENCE OF SPORES IN FIELDS

(71) Applicant: Université de Genève, Geneva (CH)

(72) Inventors: Jean-Pierre Wolf, Veyrier (CH); Jérôme Kasparian, Collonges sous Salève (FR); Vasyl Kilin, Vessy (CH)

(73) Assignee: UNIVERSITÉ DE GENÈVE, Geneva (CH)

( * ) Notice: Subject to any disclaimer, the term of this patent is extended or adjusted under 35 U.S.C. 154(b) by 589 days.

(21) Appl. No.: 17/604,460

(22) PCT Filed: Apr. 17, 2020

(86) PCT No.: PCT/EP2020/060873
§ 371 (c)(1),
(2) Date: Oct. 18, 2021

(87) PCT Pub. No.: WO2020/212577
PCT Pub. Date: Oct. 22, 2020

(65) Prior Publication Data
US 2022/0196564 A1    Jun. 23, 2022

(30) Foreign Application Priority Data

Apr. 18, 2019   (EP) .................................. 19170073

(51) Int. Cl.
*G01N 21/88* (2006.01)
*A01G 7/06* (2006.01)
(Continued)

(52) U.S. Cl.
CPC .............. *G01N 21/88* (2013.01); *A01G 7/06* (2013.01); *G01N 1/40* (2013.01); *G01N 15/0227* (2013.01);
(Continued)

(58) Field of Classification Search
CPC ... G01N 2015/0662; G01N 2015/0693; G01N 2015/0038; G01N 2015/0042;
(Continued)

(56) References Cited

U.S. PATENT DOCUMENTS 6,485,962 B1 * 11/2002 Tabacco .................... C12Q 1/04
                                                          435/808
6,498,041 B1 * 12/2002 Tabacco .................... C12Q 1/04
                                                          250/361 C
(Continued)

FOREIGN PATENT DOCUMENTS

JP        2001083079 A  *  3/2001   ......... G01N 15/0211
WO     WO-0063422 A2   * 10/2000   ............... C12Q 1/04
(Continued)

OTHER PUBLICATIONS

Tamoghna Ojha et al "Wireless sensor networks for agriculture: The state-of-the-art in practice and future challenges", Computers and Electronics in Agriculture, vol. 118, Oct. 1, 2015 (Oct. 1, 2015), pp. 66-84, XP055640113, Amsterdam, NL ISSN: 0168-1699,001: 10.1 016/j.compag.2015.08.011.
(Continued)

*Primary Examiner* — Gordon J Stock, Jr.
(74) *Attorney, Agent, or Firm* — Thomas Coester Intellectual Property

(57) ABSTRACT

The present invention relates to a system for detecting and predicting the presence of pathogens in a predetermined area of a field comprising a network of measurement stations, each measurement station comprising a first type of sensor adapted to measure environmental data, and a second type of sensor adapted to detect airborne pathogens, the system further comprising a computer processing unit adapted to collect the data to the two types of sensors and treat them by artificial intelligence to provide real-time spatially and temporally resolved data about the early detection of the patho-
(Continued)

gens as well as environmental data that are correlated to the spread and development of the pathogens and the plant disease and identify specific patterns representative of situations where treatment is required and a communication device able to send a signal to said field user indicating in which area treatment is required.

21 Claims, 10 Drawing Sheets

(51) Int. Cl.
    *G01N 1/40*      (2006.01)
    *G01N 15/0227*      (2024.01)
    *G01N 15/06*      (2024.01)
    *G01N 21/94*      (2006.01)
    *G01N 33/00*      (2006.01)
    *H04N 23/56*      (2023.01)
    *H04Q 9/00*      (2006.01)

(52) U.S. Cl.
    CPC ......... *G01N 15/0606* (2013.01); *G01N 21/94* (2013.01); *G01N 33/0027* (2013.01); *H04N 23/56* (2023.01); *H04Q 9/00* (2013.01); *G01N 2201/06113* (2013.01); *H04Q 2209/823* (2013.01)

(58) Field of Classification Search
    CPC ... G01N 2015/0046; G01N 2015/0065; G01N 2015/0088; G01N 21/84; G01N 21/85; G01N 21/8507; G01N 21/88; G01N 21/94; G01N 2021/945; G01N 1/2247; G01N 1/2273; G01N 2001/2276; G01N 2001/2285; G01N 2001/2288; G01N 2001/2291; G01N 2001/245; G01N 1/40; G01N 1/4077; G01N 15/02; G01N 15/0205; G01N 15/0211; G01N 15/0227; G01N 15/06; G01N 15/0606; G01N 15/0612; G01N 15/0618; G01N 15/0625; G01N 15/0637; G01N 15/0643; G01N 33/0027; G01N 33/0075; G01N 33/0098; G01N 33/24; G01N 2201/06113; H04Q 9/00; H04Q 2209/80; H04Q 2209/82; H04Q 2209/823; A01G 7/06; H04N 23/56
See application file for complete search history.

(56) References Cited

U.S. PATENT DOCUMENTS

| 7,418,118 | B2 * | 8/2008 | Furnas | G02B 21/365 |
| | | | | 382/128 |
| 7,622,723 | B2 * | 11/2009 | Reinisch | G01N 21/85 |
| | | | | 250/461.2 |
| 7,815,718 | B2 * | 10/2010 | Yuan | G01N 1/2208 |
| | | | | 95/218 |
| 8,331,620 | B2 * | 12/2012 | Branham | G01N 15/1463 |
| | | | | 382/103 |
| 8,372,183 | B2 * | 2/2013 | Doucette | B03C 3/70 |
| | | | | 96/26 |
| 2004/0232052 | A1 | 11/2004 | Call et al. | |
| 2006/0014300 | A1 * | 1/2006 | Maurer | G01N 15/1459 |
| | | | | 435/287.2 |
| 2016/0290912 | A1 | 10/2016 | Kent et al. | |
| 2017/0191973 | A1 | 7/2017 | Eusebi et al. | |
| 2018/0291420 | A1 * | 10/2018 | Jung | G01N 33/533 |

FOREIGN PATENT DOCUMENTS

| WO | WO-2015070986 A1 * | 5/2015 | ............ B01L 3/5055 |
| WO | 2016025848 A1 | 2/2016 | |

OTHER PUBLICATIONS

Gregory David et al "Digital holography of optically-trapped aerosol particles", Communications Chemistry, vol. 1, No. 1, Aug. 13, 2018 (Aug. 13, 2018), XP055712986,001: 10.1 038/s42004-018-0047-6.

M. L. Fall et al: "Spatiotemporal variation in airborne sporangia of Phytophthora infestans characterization and initiatives towards improving potato late blight risk estimation", Plant Pathology, vol. 64, No. 1, Jun. 6, 2014 (Jun. 6, 2014), pp. 178-190, XP0556401 04, GB ISSN: 0032-0862, 001: 10.1111 Ippa.12235.

* cited by examiner

SYSTEM AND METHOD FOR DETECTING THE PRESENCE OF SPORES IN FIELDS

TECHNICAL FIELD

The present invention relates to a system and a method for detecting the presence of spores, preferably airborne spores, in fields. More particularly, the present invention relates to a system and a method capable of accurately detecting and predicting the presence and migration of spores, preferably airborne spores, in any type of land both in real time and with high spatial accuracy.

BACKGROUND OF THE ART

The use of pesticides in agriculture has many drawbacks, with impacts on the product cost, human health, soil and air quality, as well as on the product quality. Significant efforts are therefore dedicated to reducing their use, with associated governmental regulation strategies.

Indeed, reduction of pesticides has recently become a priority because of environmental and health concerns, as well as due to additional cost for producers. Several options are considered in this respect, including genetically modified organisms, development of more "environmental friendly" pesticides, and technologies yielding more targeted spread.

One direction in this respect is to more selectively treat plantations in time and space, with the assistance of smart sensing and prediction models for smart spreading of pesticides. For "smart spreading" one can identify 4 main strategies that have been recently developed: (1) highly sensitive and selective devices, which detect pathogens in the air; (2) sampling of leaves and further analysis in the laboratory (3); modeling using meteorological data and their link to the parasite's biology and development; and (4) hyperspectral imaging of the fields from drones or satellites. To date, none of these approaches have fully qualified for the aim of significant reduction of pesticide spreads.

A major issue for (1), (2) and (3) is the spatial representativeness of the assessments over the whole production field, such data are only representative locally in space and/or time. Predictive modeling using meteorological data (air temperature and humidity, precipitation values, wind) from meteorological stations suffers from the same spatial sparsity, and thus can't be representative of local conditions like proximity to a river or forest, soil quality, shadowing, turbulence, chemical treatments, etc. Moreover, they don't assess the presence of the sources of pathogens, nor the further dissemination of the spores. Airborne (e.g. drone based) hyperspectral cameras, on the other hand, provide large scale assessments with high resolution in space (however not in time), but they detect sickness or stress of the foliage once it already occurred, lacking a satisfactory predictive information required for the producer.

Also, due to the cost of the station, existing systems do not offer the adequate coverage related to the strong spatial gradient due to field topology, which may lead to a completely different situation according to the temperature, wind force, pollution etc.

In this regard, a primary objective of the invention is to solve the above-mentioned problems and more particularly to provide a system and a method which can accurately measure the pathogen/spore concentration in several locations of a wide field area to permit the farmer of the field to accurately spread the fungicide/pesticide in a small specific location instead of the whole field.

In addition a further objective of the present invention is to provide a detector preferably to be used with the system above, for detecting and identifying the spores with a high level of discrimination of their type.

SUMMARY OF THE INVENTION

The above problems are solved by the present invention that relies on the use of a dense network (typically 1/100 m2 to 1/ha) of dedicated measurement stations, which are miniaturized and solar powered, so that they can be accommodated without hindering the agricultural processing of the field, and provide accurate real-time spatially and temporally resolved data. In other words, they provide an early detection of airborne transported pathogens, e.g. spores, as well as environmental data (soil and air temperature, leaf humidity, soil and air humidity, solar radiation, wind and turbulence, etc.) that are correlated to the spread and development of the pathogens and the plant disease.

According to an aspect of the invention, a new detector is here also described which is adapted to be used in the measurement stations to enhance the discrimination power and the identification of the types of spores.

This detector is preferably a holographic lensless microscope permitting an identification of the nature of the spores which are in the area of the measurement station.

According to a preferred embodiment, the holographic microscope comprises a thin transparent blade of less than 1 mm thickness (e.g. made of sapphire), preferably having a disc shape, which is mounted on a stepper motor able to rotate the blade. The microscope further comprises cleaning pads adapted to clean specific areas of the blade and a conductive pad in contact with the blade adapted to discharge static electricity on the blade's surface. Thanks to this arrangement, the new spores are always deposited on a fresh and cleaned surface because the investigated area of the surface first receives the spores, permits imaging immediately after (or even simultaneously) and is then displaced (because of rotation) to be wiped by the pad to present a fresh and clean new area for the next spores to be collected.

The blade is preferably disposed in a casing which presents an opening in regard of the blade such that the light source, preferably a laser, even more preferably a 405 or 515 nm laser, can emit a light directly on the blade to illuminate the spores deposited onto the blade's surface.

In order to capture images of the illuminated spores on the blade, the microscope further comprises an image capturing device such as a CMOS camera, which is preferably placed in front of the opening on the other side of the blade so as to be able to capture images of the spores immediately after deposition and illumination.

According to a preferred embodiment, the air around the detector is sucked by a fan such that the particles are softly deposited on the rotating blade, which is preferably a sapphire disc, which is rotated by a stepper motor. These particles are illuminated by the laser and holographic images of them are formed on the camera surface, which sends the image data to a processing unit using an AI software to recognize the spores.

These data are treated by artificial intelligence (machine learning) to identify specific patterns representative of situations where treatment is required. The large quantity of spatiotemporally resolved data are then transmitted to a main station, which processes the information with AI. The target objective for the AI fitness function can be defined by a specific campaign of sampling with high spatial resolution and/or as continuous sampling on filters, which are subsequently analysed in the laboratory by microscopy, by polymerase chain reaction (PCR), optical shape recognition, and/or spectroscopy on particles impacted on filters, with a daily to weekly integration times, etc. Once the data pattern representative of the target is identified, no further calibration is required, although each additional further data acquisition will participate to the fine tuning (learning curve) of the AI identified pattern. The network is then fully operational, and early warnings can be provided to the producers, at high spatial and temporal resolution. This allows the producer, for instance, to decide to spray pesticides only on a very limited fraction of the field and thus prevent further spread of the spores while minimizing the use of pesticides.

The solution proposed here is, therefore, a network of low cost and stand-alone stations, interconnected, providing real-time information, and deployed over the whole field.

The measurement stations provide data such as the concentration, size and morphology of atmospheric aerosol particles (centered on the sizes of spores or other expected contaminants, like bacteria), the air and soil temperature, solar irradiance, air humidity, leaf wetness, leaf size and leaf motion.

The algorithm also takes into account the state of the art knowledge of the biology and growth of the pathogens, to restrict the parameter space. Results are sent (e.g. by SMS or e-mail, or provided through a mobile application and web platform) to farmers, as maps of infection risk, several days in advance to allow them to plan and achieve a spatially-targeted treatment.

Furthermore, an individual station is sufficiently compact to be installed on a drone, allowing to cover a wide area and perform both pathogen detection and treatment with high spatial accuracy, if required.

BRIEF DESCRIPTION OF THE DRAWINGS

Further particular advantages and features of the invention will become more apparent from the following non-limitative description of at least one embodiment of the invention which will refer to the accompanying drawings, wherein FIG. 1 schematically represents the spores monitoring and environment parameters acquisition stations of the present invention;

FIG. 3 shows a scheme of a typical decision-making algorithm of the present invention;

FIG. 4 shows a possible network deployment in vineyards;

DETAILED DESCRIPTION OF THE INVENTION

The present detailed description is intended to illustrate the invention in a non-limitative manner since any feature of an embodiment may be combined with any other feature of a different embodiment in an advantageous manner.

Figure 1:
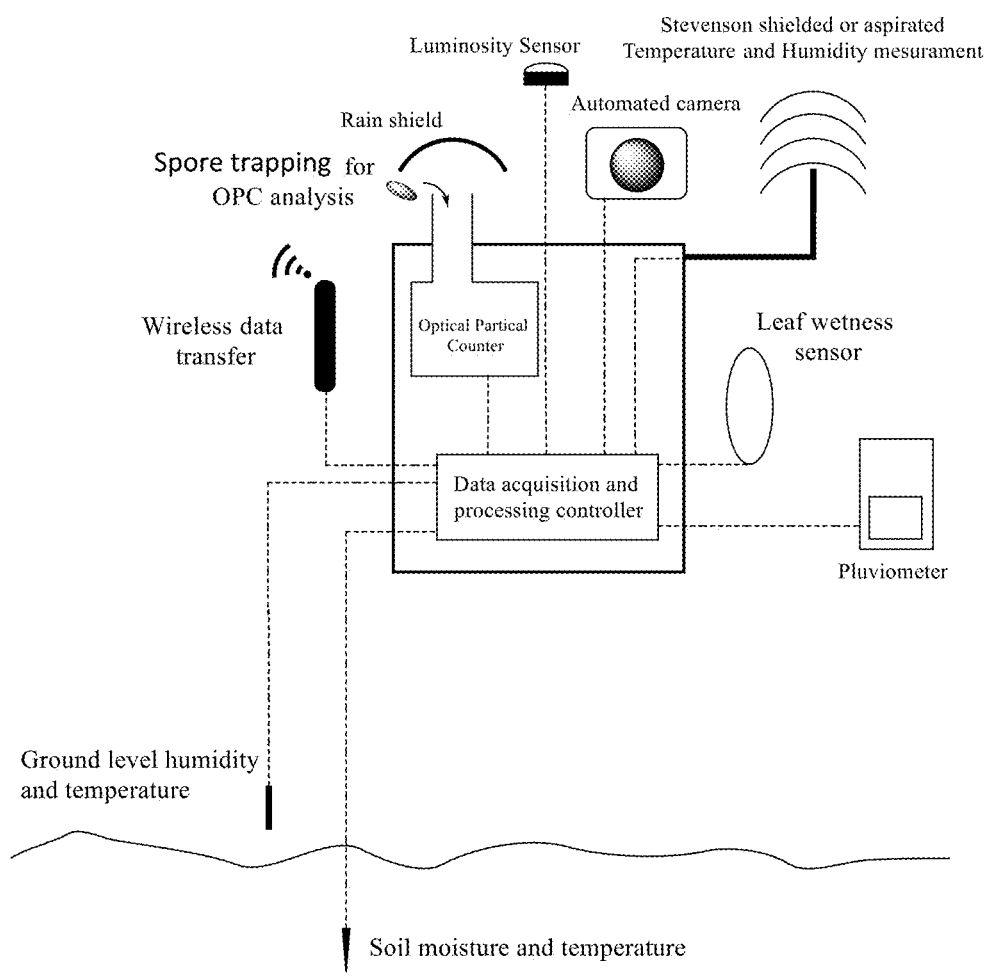

FIG. 1 shows a first aspect of the invention which is a measurement station for real-time and spatially resolved monitoring of spores. This measurement station combines various types of sensors for measuring environmental parameters combined with detectors of airborne spores. Environmental sensors typically include, but are not limited to, the temperature of the soil, temperature near the ground, temperature of the air at the leaf level, humidity near the ground, soil moisture, humidity of the air at the station level, leaf wetness sensor, rainfall monitoring, and sunlight sensor.

The measurement stations, in order to enhance the accuracy of the measurements preferably comprise a holographic microscope permitting an identification of the nature of the spores which are in the area of the measurement station.

Figure 11:
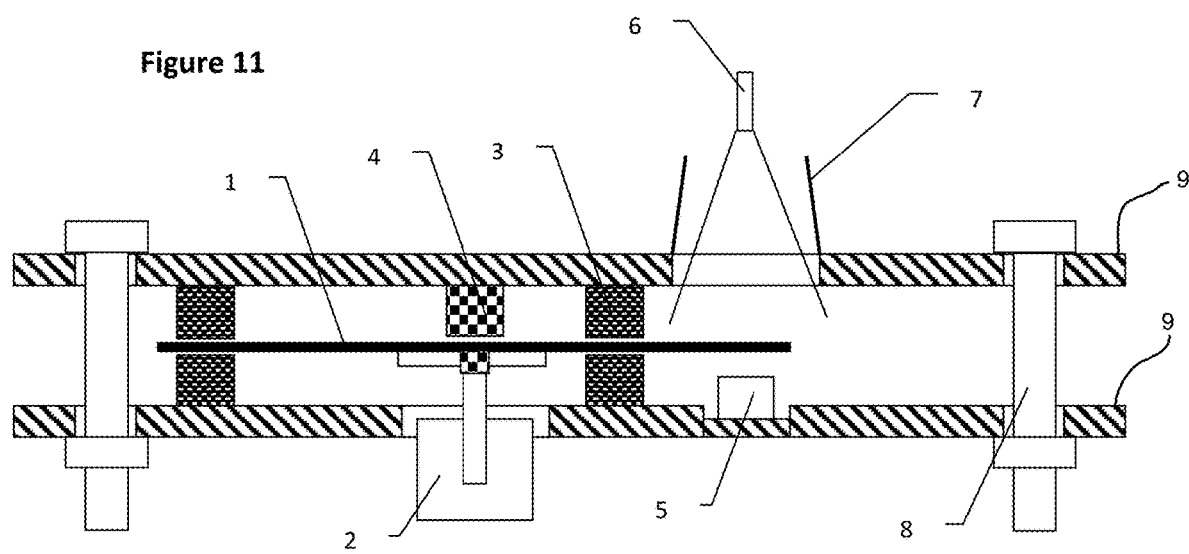
FIG. 11 shows a schematic representation of the holographic microscope used as detector according to the present invention.

The holographic microscope is represented in FIG. 11 and comprises a sapphire blade 1, preferably having a disc shape, which is mounted on a stepper motor 2 able to rotate the blade 1. The microscope further comprises at least one, preferably more, cleaning pad 3 adapted to clean specific areas of the blade 1 and a conductive pad 4 in contact with the blade adapted to discharge static electricity generated on the blade's surface. The blade is preferably disposed in a casing which presents an opening in regard of the blade 1 such that the light source 6, preferably a laser, even more preferably a 405 or 515 nm laser, can emit a light directly on the blade to illuminate the spores deposited onto the blade's surface. Preferably, the opening is surrounded by a protecting wall 7 permitting to limit stray light.

In order to capture images of the illuminated spores on the blade, the microscope further comprises an image capturing device 5 such as a CMOS camera, which is preferably placed in front of the opening on the other side of the blade so as to be able to capture images of the spores immediately after deposition and illumination.

The cleaning pads 3 are clamping the disc. In order to have a proper clamping pressure, the detector is provided with screws 8 which can modify the distance between the two supports 9 and thereby adapted the clamping pressure.

Thanks to this arrangement, the air around the detector is sucked by a fan such that the particles are sent into the detector and deposited on the rotating blade, which is preferably a sapphire disc which is rotated by a stepper motor. Then they are illuminated by the laser and holograms of these particles are taken by the camera, which sends the image data to a processing unit using an AI software to recognize the spores.

Further, an additional automated camera is used to acquire information about the motion of the leaves, the area of the leaves and their growth dynamics, and about the treatments with fungicides applied to the field. In addition to the holographic detector, additional spores detectors can be installed in the station which could, for example, be any detector which provides information about spore's presence based on physical detection through any suitable method. These additional spore detectors could consist in automated mobile microscopes, fluorescence-based detectors, light scattering particle detectors, and similar detectors which allows real-time detection of airborne particles. In addition, in a preferred embodiment, the station may also comprise optical particle counters (OPC) which are used to provide information about the size and the number density of spores in the air. All the data acquired by each station of the network of stations are processed by control electronics and sent to a remote server.

Figure 2:
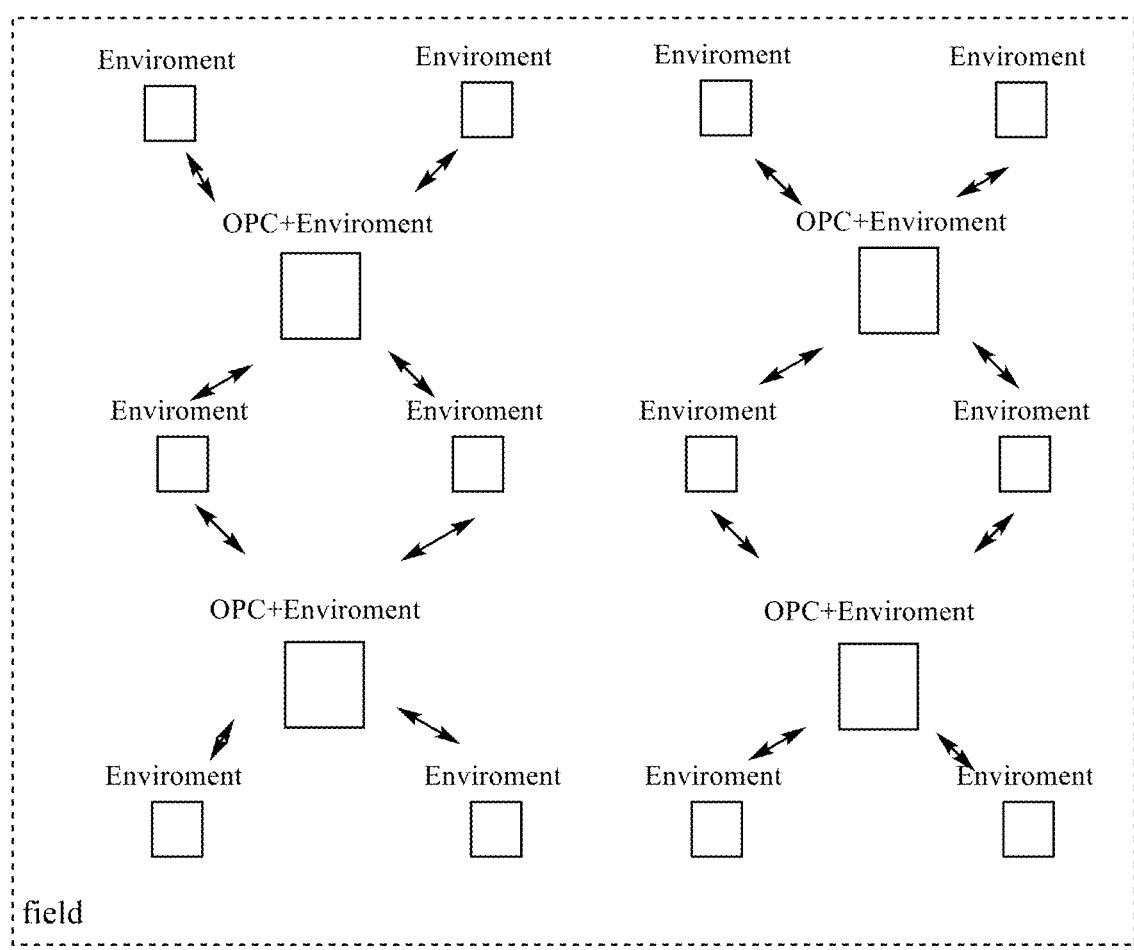
FIG. 2 represents a first embodiment of a deployment of the Optical Particle Counter (OPC) equipped stations and supporting environment monitoring stations.

According to a preferred embodiment of the invention, a system is provided comprising a plurality of these stations that are deployed as a network in target fields for data collection and where some stations also serve as a master collecting the data collected by a smaller station which monitor environment parameters only as shown in FIG. 2.

Detection of spores using a network of static stations has the advantage of noninvasive monitoring of spore-bearing movement of air masses in contrast to methods based on drones. A network of spore detectors combined with monitoring of environment parameters favorable to pathogens growth allows monitoring dynamics of spore-bearing air masses without introducing bias of passive spore traps. This bias is caused by trapping spores independently from environment parameters using impactor filters, sticky tapes or glue covered surfaces. Such a passive collection of spores leads to overestimation of the infection risk.

Figures 3, 4:
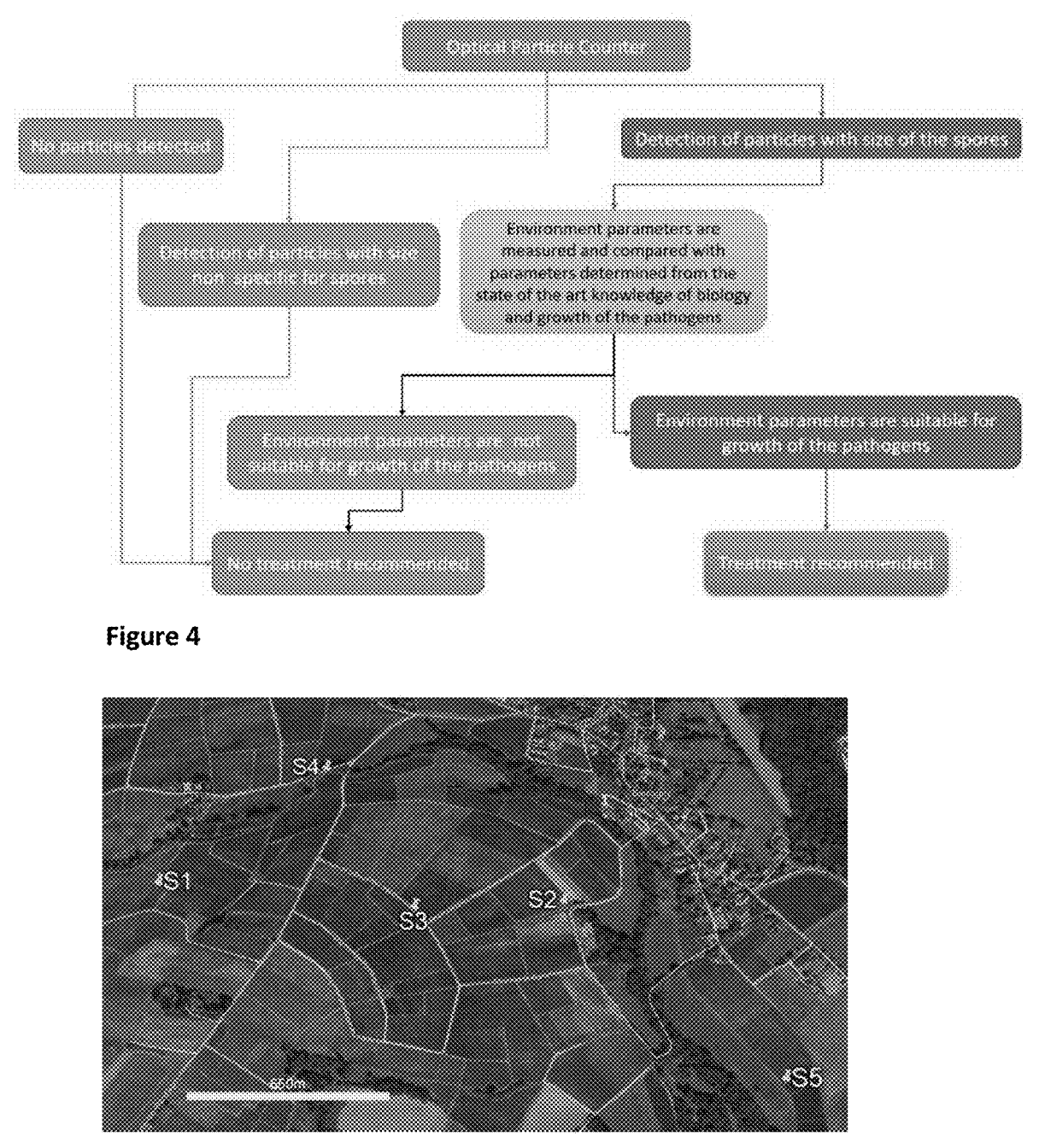

In the present embodiment, the recommendation for application of fungicides is formed by an AI algorithm executed as shown in FIG. 3. Upon detection of increasing concentration of the spores in the air, application of preventive anti-germination fungicides is recommended. Additionally, the system verifies if environmental parameters observed during up to 3 days before spores' detection are suitable for spore's attachment on the leaf based on temperature, humidity and leaf moisture parameters. The probability of spore's deposition on leaves is also evaluated using information about last treatment and occurrence of rain. When spores are detected to be attached/germinating on the leaves, the system monitors environmental and leaf parameters suitable for incubation and mycelium increase and at this step application of anti-mycelium fungicides is recommended. Next, the system controls and evaluates when environment parameters are detected as favorable for sporulation. In this case, treatment is recommended using anti-sporulation fungicides. After a sufficient amount of cycles and when after treatment sessions, no significant increase in spores was detected locally only/mostly anti-germination (infection preventing) fungicides could be used upon detection of spores in the air. Moreover, the algorithm can be adjusted if the treatment strategy is based on applying fungicides which are targeting germination, mycelium spread, sporulation or another mechanism explicitly. Also, information about the last treatment is used to evaluate fungicides efficiency and can optionally be later added into the AI model for further improvement of the treatment strategy. This adjustment is valuable because of the variations in efficiency of applied fungicides caused by different chemicals and spreading techniques, rain washing, and the field topography, such as terrain flatness and the height of the plants. The spatial resolution required for optimized prediction is determined for each field and could be adjusted iteratively through feedback between detection of sporulation events and their occurrence after applying fungicides. The spatial and temporal resolution of sporulation events combined with information about local turbulence is used to provide a recommendation for the application of fungicides at locations of the infection sources and locations into which spores will predictably spread. An automated camera is used for monitoring the growth of new leaves in order to reapply fungicides on them in a preventive manner. Detection of strong leaves motion is used as an indicator of the increased probability of spores spread. Rainfall information is used for monitoring the washing out of previously applied fungicides. The number of environment parameters could be extended according to improvements of state-of-the-art knowledge of the biology of the pathogens and such parameters could be combined with airborne spores monitoring.

SPECIFIC EXAMPLE

Figure 5:
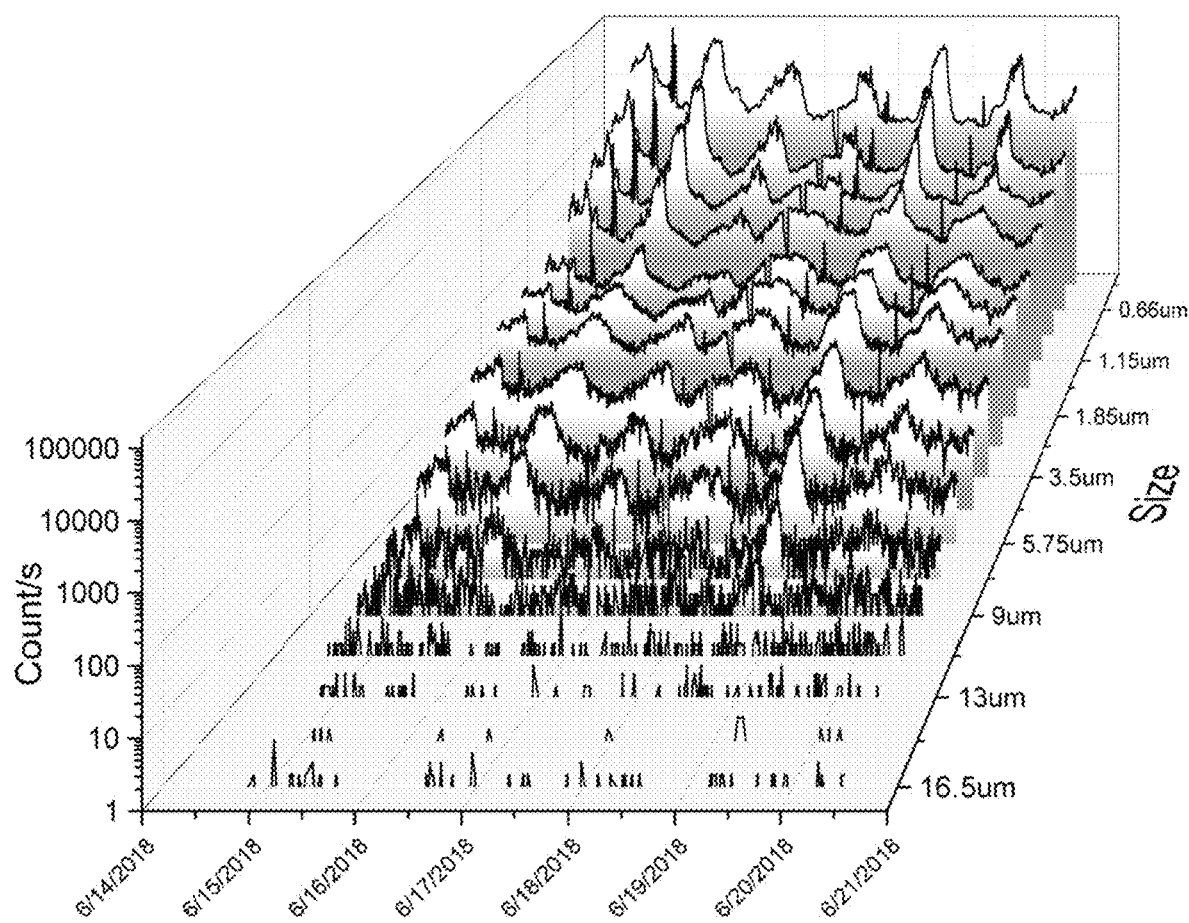
FIG. 5 is a size and time-resolved particles detection by OPC over five days acquired by station number S5 shown in FIG. 4.

According to the first example of implementation of the invention, five stations were deployed in a field as shown in FIG. 4. The Optical particle counters (OPC) in the stations monitored spores of various sizes over an extended period as shown in FIG. 5.

Figure 6A:
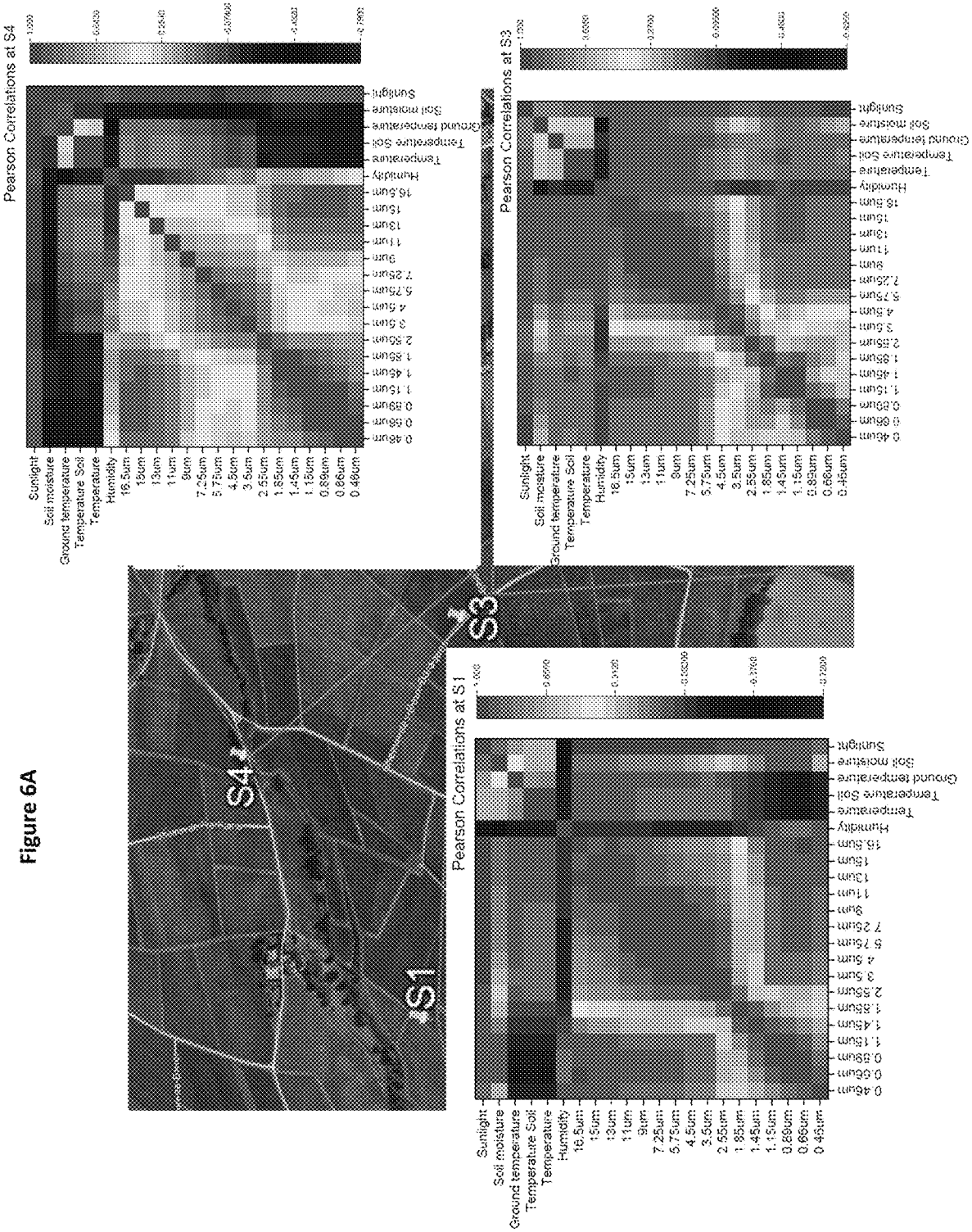
FIG. 6A represents diagrams of Pearson's correlations between monitored parameters for stations number S1, S4 and S3 shown in FIG. 4.
Figure 6B:
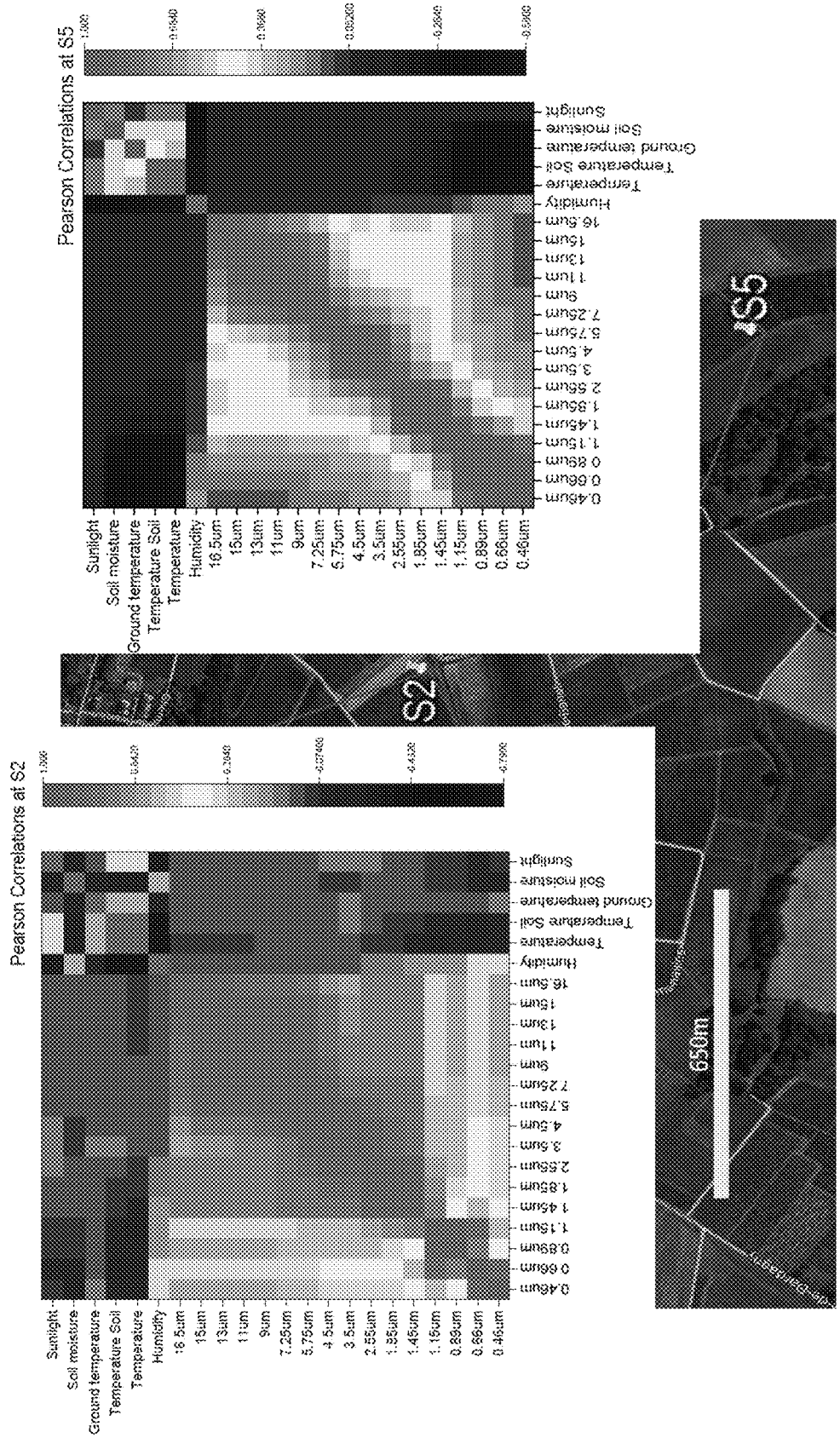
FIG. 6B represents diagrams of Pearson's correlations between monitored parameters for stations S2 and S5 shown in FIG. 4.

The species occurrence at the station was explored by performing a Pearson's correlation analysis as represented in FIG. 6A and FIG. 6B. From this analysis, at least three families of particles were detected. The first one with a maximum size of 2.55 µm, is observed at all five stations and correspond to the presence of dust and background aerosols at all positions. A second family with a size in the range of 3.5-7.25 µm which was also observed at all stations and is explained by the presence of spores specific for other plants such as Chaetomium, Agrocybe, Xylariaceae, Helicoma, Paraphaeosphaeria. The third family of spores was observed with characteristic sizes in a range from 9-16.5 µm or bigger which is comparable with the size of Plasmopara Viticola (PV, downy mildew's pathogen) which was, in the present case, the monitored one since this spore is detrimental to vineyards.

Moreover, correlation maps demonstrate that environmental parameters and detected spores are not correlating in the same manner across all stations. The sampling range of spore's sizes could be extended using suitable OPCs. Detected size is attributed to the spores of specific species in a field-personalized manner by using a correlation between sporulation environmental conditions and suitable for growth environment parameters to exclude errors in spore sizing caused by biodiversity.

Figure 7:
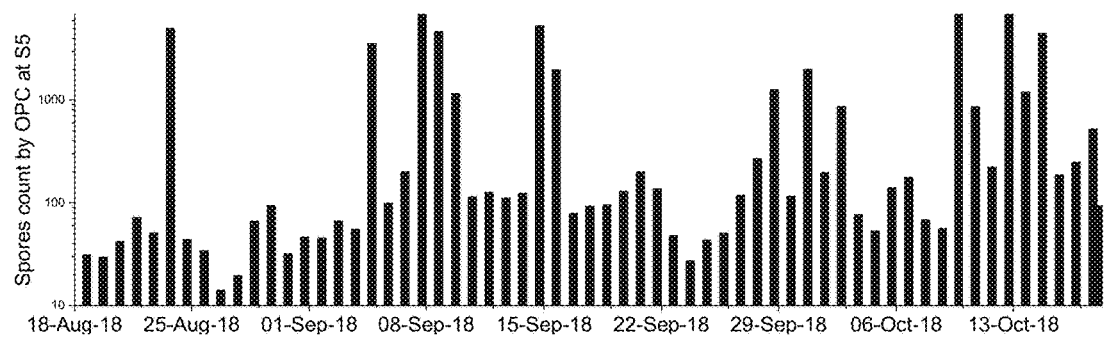
FIG. 7 represents daily counts of spores with size 9-15 µm collected at station number S5 shown in FIG. 4.

The daily count of spores detected by OPCs is used for sporulation events detection as shown in FIG. 7. In the present example sporulation events are extracted from spore's concentration dynamics using local maxima for each station.

Figure 8:
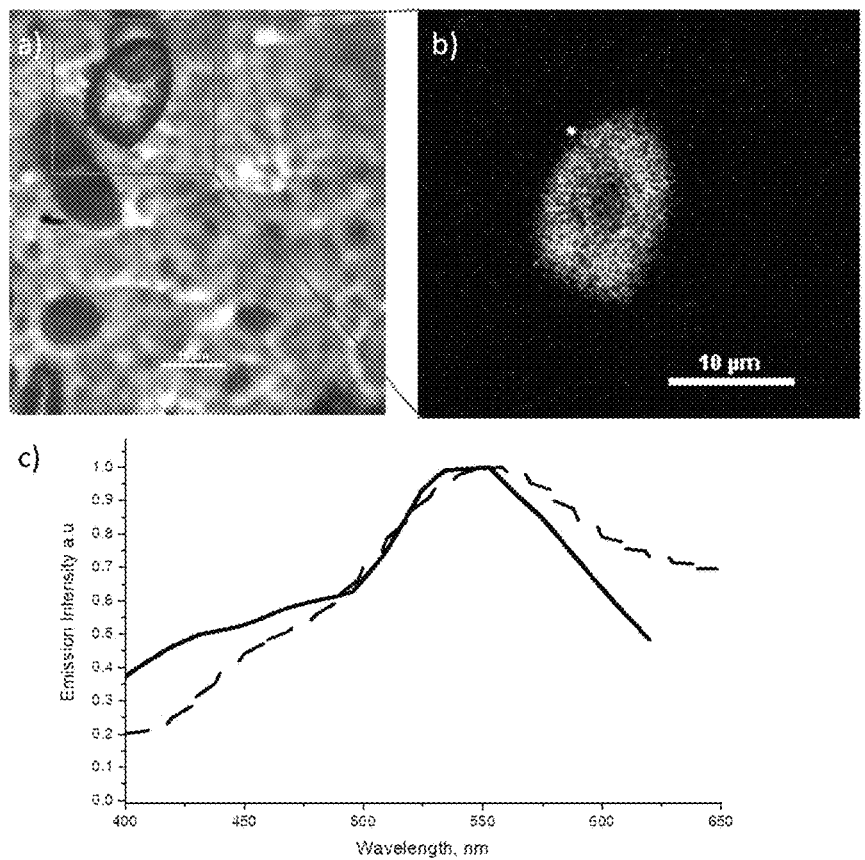
FIG. 8 shows Bright-field images a) and laser-induced autofluorescence image b) of Plasmapora Viticola (PV) imaged on impactor filters. Autofluorescence spectra c). A solid line is spectra of PV reported by Below et al. for PV in leaves and dashed line is a typical spectrum recorded from PV trapped on filters as in the present invention.

The sporulation event occurrence was controlled using an additional station positioned next to S5 station. This additional station impacted airborne spores on filters suitable for microscopy study. FIG. 8 shows a Microscopy study that was carried out on a Nikon multiphoton inverted microscope (A1R-MP). Imaging were performed on a Nikon multiphoton inverted microscope (A1R-MP) coupled with a Mai-Tai tunable Ti:sapphire oscillator from Spectra-Physics (100 fs, 80 MHz, 700-1000 nm). A Plan APO 20×WI N.A. 0.75 objective was used to focus the excitation 720 nm and to epi-collect the autofluorescence signal. The collected signal was processed by a Nikon AI descanned spectrometer. The signal was collected and directed through an optical fiber to the spectral detector, where it was diffracted by a grating and projected on a 32-PMT array. The working range in detection was 400 nm to 650 nm and the resolution was set to 10 nm for a total of 25 independent detection channels.

Figure 9:
FIG. 9 shows sporulation events in the field, detected during 3-17 Oct. 2018. The map with red circles representing the total amount of sporulation events during the period. The diameter of circles are normalized by the number of events.
Figure 9:
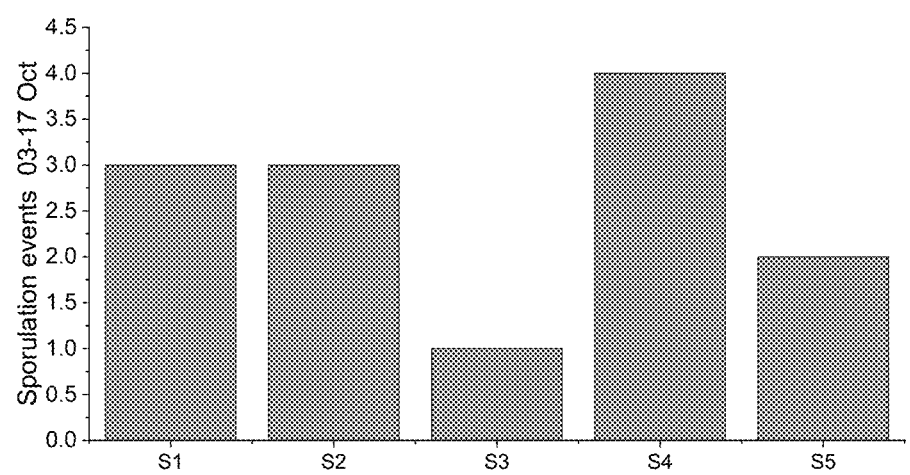
Figure 10A:
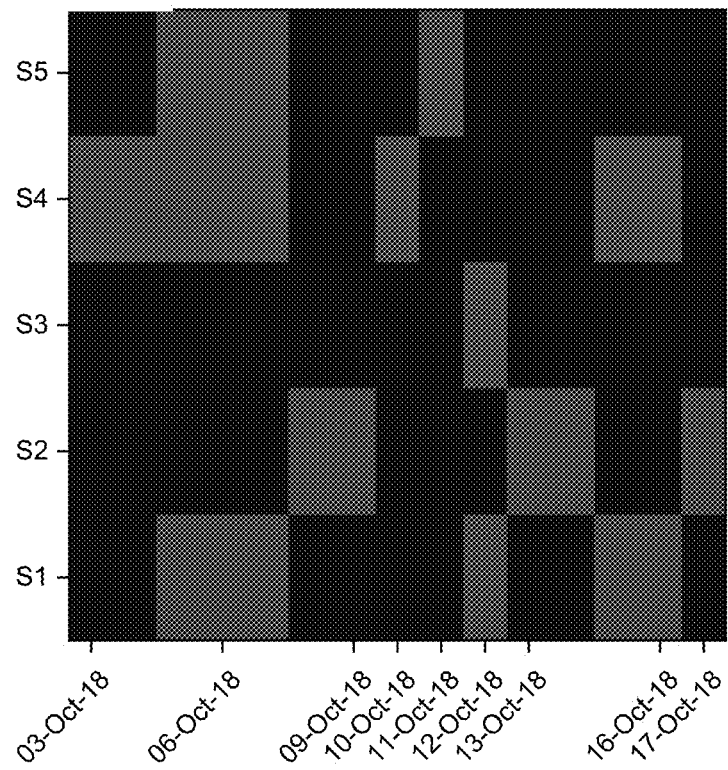
FIG. 10A shows sporulation events detected by stations extracted from daily counts of species with size 9-15 µm.
Figure 10B:
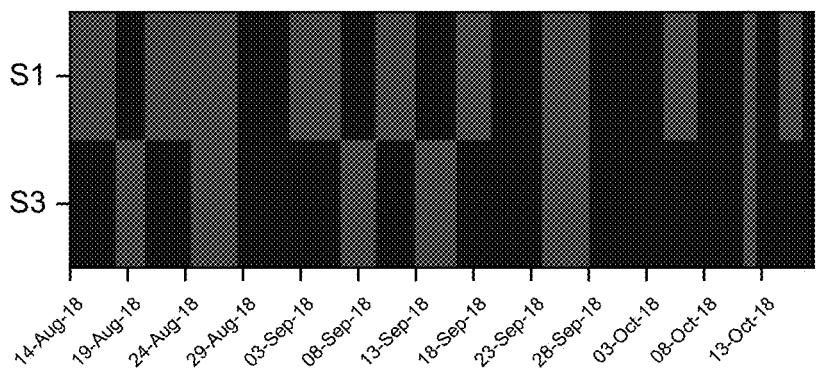
FIG. 10B shows sporulation events detected by S1 and S3 stations extracted from daily counts of species with size 9-15 µm.

As we can see from FIG. 9, the detected sporulation events are strongly position dependent. Furthermore, as we can see from FIGS. 10A and 10B, they are not synchronized in time.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure.

The invention claimed is:

1. Measurement station for detecting a presence of pathogens in a predetermined area, said station comprising a spore detecting device wherein said device comprises:
    a recording surface adapted to receive spores onto its surface,
    a light source, adapted to illuminate the spores deposited onto the recording surface, and
    an imaging device adapted to capture image data of the illuminated spores,
    characterized in that the recording surface is a transparent thin blade adapted to be rotated by a motor and placed between said light source and said imaging device.

2. Measurement station according to claim 1 wherein the transparent thin blade is made of sapphire.

3. Measurement station according to claim 1 being equipped with a communication system adapted to transfer the collected image data from stations to a cloud service and/or to a remote computer.

4. Measurement station according to claim 1, wherein the blade has a disc shape.

5. Measurement station according to claim 1, wherein the motor is a stepper motor.

6. Measurement station according to claim 1 wherein the thin transparent blade is a sapphire glass blade, further comprising at least one cleaning pad clamping said sapphire glass blade so as to be able to clean specific areas of the blade upon rotation.

7. Measurement station according to claim 1, further comprising a clamping pressure modifying element.

8. Measurement station according to claim 7, wherein the clamping pressure modifying element comprises screws which can modify a distance between two supports housing the blade and at least one cleaning pad.

9. Measurement station according to claim 1, further comprising a carbon pad adapted to discharge static electricity generated on the blade's surface.

10. Measurement station according to claim 9, wherein the carbon pad is located on a center of the blade.

11. Measurement station according to claim 1, wherein the imaging device is a CMOS camera.

12. Measurement station according to claim 1, wherein the light source is a laser.

13. Measurement station claim 1, wherein the spore detecting device is a holographic microscope.

14. Measurement station according claim 1, further comprising an automated camera used to acquire information about motion of the leaves, an area of the leaves and their growth dynamics.

15. Measurement station according to claim 14, wherein the automated camera is also adapted to acquire information about previous treatments with fungicides applied to a specific area of a field.

16. Measurement station according to claim 1, further comprising additional detectors comprising any of automated mobile microscopes, fluorescence-based detectors, light scattering particle detectors, and detectors which allow real-time detection of airborne particles for providing information about a size and a number density of spores in an environment.

17. System for detecting and predicting in real time a presence of pathogens in a predetermined agricultural area comprising a network of measurement stations each station having a spore detecting device including a recording surface adapted to receive spores onto its surface, a light source, adapted to illuminate the spores deposited onto the recording surface, and an imaging device adapted to capture image data of the illuminated spores, characterized in that the recording surface is a transparent thin blade adapted to be rotated by a motor and placed between said light source and said imaging device, the system comprising:
    some stations being adapted for detection of airborne pathogens;
    some stations being adapted for the acquisition of environmental parameters;
    at least one of the above stations being adapted for simultaneous detection of airborne pathogens and for the acquisition of environmental parameters;
    the system further comprising
    a computer processing unit adapted to collect data from both the detection of airborne pathogens and the acquisition of environmental parameters and to analyze them by artificial intelligence to provide real-time spatially and temporally resolved data about the presence of pathogens as well as environmental data that are correlated to a spread and development of the pathogens and a plant disease and identify specific patterns representative of situations where treatment is required; and
    a communication device able to send information to a user, indicating in which area treatment is required.

18. System according to claim 17, characterized in that the environmental data comprises at least one of soil temperature, temperature near a ground level, temperature of air at a level of leaves, humidity near the ground level, leaf humidity, soil moisture, humidity of air at a station level, solar radiation, wind, turbulence and rainfall.

19. System according to claim 17, characterized in that the pathogens are airborne transported pathogens in an agricultural field.

20. System according to claim 19, characterized in that the airborne transported pathogens are Plasmopara Viticola.

21. Method for detecting and predicting a presence of pathogens in a predetermined geographic area of a field using a system having a network of measurement stations, each station having a spore detecting device including a recording surface adapted to receive spores onto its surface, a light source, adapted to illuminate the spores deposited onto the recording surface, and an imaging device adapted to capture image data of the illuminated spores, characterized in that the recording surface is a transparent thin blade adapted to be rotated by a motor and placed between said light source and said imaging device, the system including: some stations being adapted for detection of airborne pathogens; some stations being adapted for the acquisition of environmental parameters; at least one of the above station being adapted for simultaneous detection of airborne pathogens and for the acquisition of environmental parameters; the system further including: a computer processing unit adapted to collect the data from both the detection of airborne pathogens and the acquisition of environmental parameters and to analyze them by artificial intelligence to provide real-time spatially and temporally resolved data about the presence of pathogens as well as environmental data that are correlated to a spread and development of the pathogens and a plant disease and identify specific patterns representative of situations where treatment is required; and a communication device able to send information to a user, indicating in which area treatment is required, the method, characterized in that it comprises:

a first measuring step comprising measuring the environmental data, a second measuring step comprising measuring pathogens presence, a data collecting and sending step, adapted to collect data of the two measuring steps and sending them to the CPU, a data treatment step adapted to treat the data by artificial intelligence to provide real-time spatially and temporally resolved data about an early detection of the pathogens as well as environmental data that are correlated to the spread and development of the pathogens and the plant disease and the identified specific patterns representative of situations where treatment is required and a communication step for sending a warn signal to the user indicating in which area treatment is required, if required.

\* \* \* \* \*